United States Patent [19]

Grohe

[11] Patent Number: 4,844,902

[45] Date of Patent: Jul. 4, 1989

[54] TOPICALLY APPLICABLE FORMULATIONS OF GYRASE INHIBITORS IN COMBINATION WITH CORTICOSTEROIDS

[75] Inventor: Klaus Grohe, Odenthal, Fed. Rep. of Germany

[73] Assignee: Bayer Aktiengesellschaft, Leverkusen, Fed. Rep. of Germany

[21] Appl. No.: 154,835

[22] Filed: Feb. 11, 1988

[30] Foreign Application Priority Data

Feb. 17, 1987 [DE] Fed. Rep. of Germany ....... 3704907

[51] Int. Cl.$^4$ ............................................. A61F 13/00
[52] U.S. Cl. ..................................... 424/449; 424/447
[58] Field of Search ......................................... 424/449

[56] References Cited

U.S. PATENT DOCUMENTS 4,659,603 4/1987 Groke et al. ...................... 514/254
4,681,876 7/1987 Marpla et al. ...................... 514/182

OTHER PUBLICATIONS

BE-A- 829 197 (L. Grosjean).
GB-A-2 116 425 (Rhom Pharma).
Embase 86048074, 0150500902110.

*Primary Examiner*—Ellis P. Robinson
*Assistant Examiner*—Leon R. Horne
*Attorney, Agent, or Firm*—Sprung Horn Kramer & Woods

[57] ABSTRACT

Topically applicable formulations comprising known ciprofloxacin-type antibacterials of the formula

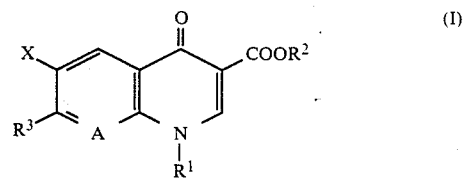

in which A is N or C-R$^9$, and corticosteroids are especially effective in therapy, particularly in the oral cavity. The formulations can be used in the form of plasters, gels, suspensions, emulsions and solutions.

11 Claims, No Drawings

TOPICALLY APPLICABLE FORMULATIONS OF GYRASE INHIBITORS IN COMBINATION WITH CORTICOSTEROIDS

The invention relates to topically applicable formulations which contain, as active compounds, antibacterially active compounds which belong to the group of gyrase inhibitors and have the general formula

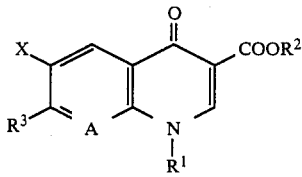

in which
R$^1$ represents methyl, ethyl, propyl, isopropyl, cyclopropyl, vinyl, 2-hydroxyethyl, 2-fluoroethyl, methoxy, amino, methylamino, dimethylamino, ethylamino, phenyl, 4-fluorophenyl and 2,4-difluorophenyl,
R$^2$ represents hydrogen, alkyl with 1 to 4 carbon atoms or (5-methyl-2-oxo-1,3-dioxol-4-yl)-methyl,
R$^3$ represents methyl or a cyclic amino group, such as

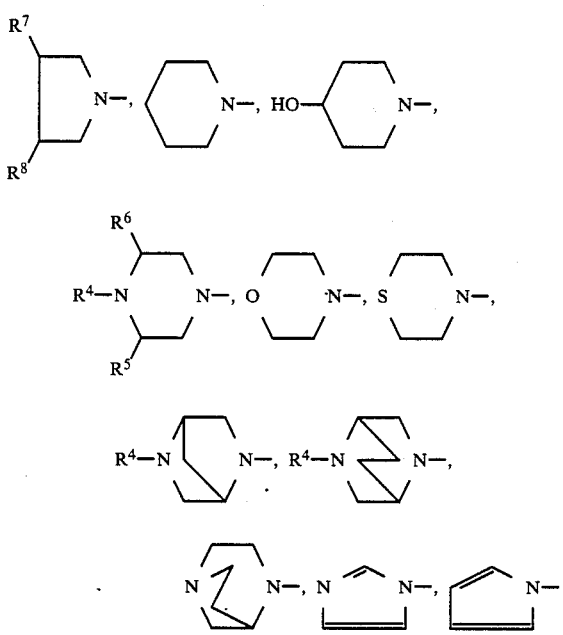

wherein
R$^4$ represents hydrogen, alkyl with 1 to 4 carbon atoms, 2-hydroxyethyl, allyl, propargyl, 2-oxo-propyl, 3-oxobutyl, phenacyl, formyl, CFCL$_2$-S-CFCL$_2$-SO$_2$-, CH$_3$O-CO-SO-, benzyl, 4-aminobenzyl or

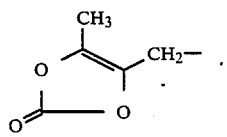

R$^5$ represents hydrogen or methyl,
R$^6$ represents hydrogen, alkyl with 1 to 4 carbon atoms, phenyl or benzyloxymethyl,
R$^7$ represents hydrogen, amino, methylamino, ethylamino, aminomethyl, methylaminomethyl, ethylaminomethyl, dimethylaminomethyl, hydroxyl or hydroxymethyl and
R$^8$ represents hydrogen, methyl, ethyl or chlorine,
X represents hydrogen, fluorine, chlorine or nitro and
A represents N or C-R$^9$,
wherein
R$^9$ represents hydrogen, halogen, such as fluorine or chlorine, methyl or nitro, or
A, together with R$^1$, can also form a bridge with the structure

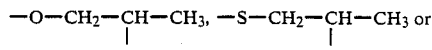

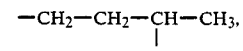

and a corticosteriod or several corticosteroids.

The gyrase inhibitors can be used in the topically applicable formulations as such or as a salt with an acid or base. Use as a prodrug, for example of esters, is also possible.

The gyrase inhibitors are applied topically in combination with corticosteriods in the form of the topically applicable formulations for the treatment or prophylaxis of infections, diseases and injuries to the skin, including burns. Treatment or prophylaxis of deeplying or systemic infections is also possible by topical application or gyrase inhibitors.

The topically applicable formulations according to the invention contain 0.05 to 30% preferably 0.05 to 20% by weight of active compound of the formula (I) and corticosteroids.

The topically applicable formulations according to the invention particularly preferably contain 0.1 to 5% by weight of active compound of the formula (I) and topicallys.

The formulations mentioned contain, in particular, ciprofloxacin, norfloxacin, pefloxacin, amifloxacin, pirfloxacin, ofloxacin and/or enoxacin.

The corticosteroid active compounds which are used in the formulations according to the invention are known. Such active compounds are described in detail, for example, in Miller, Zunro, Dengs 19, 119-134 (1980) and Wolfe, Bayer's Medicinal Chemistry 3 4A Ed., John Wiley and Bus, New York, N.Y. pages 1273-1316, 917-1309 (1981).

Other corticosteroid active compounds which are suitable as constituents of the formulations according to the invention are described in: European Pat. No. 0,036,138, European Pat. No. 0,129,283, European Pat. No. 0,098,566, European Pat. No. 0,173,478, European Pat. No. 0,136,586, European Pat. No. 0,098,568, European Pat. No. 0,095,894, European Pat. No. 0,078,235, European Pat. No. 0,023,713, German Pat. No. 3,227,312, German Pat. No. 3,243,482, German Pat. No. 3,401,680, German Pat. No. 3,400,188, U.S. Pat. No. 4,257,969 and U.S. Pat. No. 4,343,798.

Preferred corticosteroids are hydroxytriamcinol-one, α-methyl-dexamethasone, β-methyl-betamethasone, beclomethasone, α-propionate, betamethasone bonzoate, betamethasone dipropionate, betamethasone valerate, clobetasol valerate, desonide, desoxymethasone, dexamethasone, diflorasone diacetate, diflucortolone valerate, flurandrenolone, fluclorolone acetonide, flumethasone pivalate, flucinolone acetonide, fluocinonide, fluocortin butyl ester, fluocortolone, fluprednidene acetate, flurandrenolone, halcinonide, hydrocortisone acetate, hydrocortisone butyrate, methylprednisolone, triamcinolone acetonide, cortisone, cortodoxone, flucetonide, fludrocortisone, diflorasone diacetate, fluradrenolone acetonide, medrysone, amcinafal, amcinafide, betamethasone and esters thereof, chloroprednisone, clocortolone, clescinolone, dichlorisone, difluprednate, flucloronide, flunisolide, fluoromethalone, fluperolone, fluprednisolone, hydrocortisone, meprednisone, paramethasone, prednisolone, prednisone and beclomethasone dipropionate.

Mixtures of the so-called corticosteroids are also possible constituents of the formulations according to the invention.

Examples, in preferred % by weight, of the corticosteroids which can be used according to the invention are, in particular:

A beclomethasone dipropionate 0.5%
B clobetasol propionate 0.05%
C diflucortolone valerate 0.3%
D fluocinolone acetonide 0.2%
E beclomethasone dipropionate 0.025%
F betamethasone benzoate 0.025%
G betamethasone dipropionate 0.05%
H betamethasone valerate 0.1%
I desonide 0.05%
J desoxymethasone 0.25%
K diflorasone diacetate 0.05%
L diflucortolone valerate 0.1%
M fluclorolone acetonide 0.025%
N fluocinolone acetonide 0.025%
O fluocinonide 0.05%
P fluocortolone 0.5%
Q fluprednidene.(fluprednylidene) acetate 0.1%
R flurandrenolone 0.05%
S halcinonide 0.1%
T hydrocortisone butyrate 0.1%
X triamcinolone acetonide 0.1%
Y clobetasone butyrate 0.05%
Z flumethasone pivalate 0.02%
$A^1$ fluocinolone acetonide 0.01%
$B^1$ fluocortine butyl ester 0.75%
$C^1$ fluocortolone 0.2%
$D^1$ flurandrenalone 0.0125%–0.025%
$E^1$ hydrocortisone (urea) 1%
$F^1$ dexamethasone 0.01%
$G^1$ hydrocortisone (alcohol or acetate) 0.1%–1%
$H^1$ methylprednisolone 0.25%

Corticosteriods from the group consisting of triamcinolone acetonide, hydrocortisone acetate, betamethasone valerate, fluocinolone acetonide, flupamesone and mixtures of these compounds are particularly preferred.

Other preferred active compounds are desoxycorticosterone, fludrocortisone, hydrocortisone, betamethasone, cortisone, dexamethasone, prednisolone, prednisone, methylprednisolone, paramethasone, triamcinolone and mixtures of these compounds.

The formulations according to the invention contain the corticosteriods in amounts of 0.01 to 10% by weight, preferably 0.02 to 5% by weight and particularly preferably 0.05 to 5% by weight.

A. General section

The topical formulations of the invention include solutions, sprays, lotions, gels, ointments, creams, powders, dusting powder sprays, pastes, suspensions, emulsions, foams and sticks containing the active compound of the formula I, and if appropriate also several active compounds.

The present compounds of the formula I can also be applied topically in the form of plasters, spray plasters, occlusive dressings, compresses and controlled release systems. These formulations can contain the active compounds in dissolved or suspended form.

Ointments contain, as the base, hydrocarbon gels, lipogels, absorption bases, water-in-oil ointment bases, mixed emulsions or polyethylene glycols.

Creams contain oil-in-water bases.

Pastes contain, in addition to an ointment or cream base, high amounts of pulverulent constituents, such as zinc oxide, talc, starch or titanium dioxide.

Gels contain solvents, such as water, ethanol, isopropanol or propylene glycol, and are prepared using gelling agents, such as cellulose ethers, alginates, polyacrylates, bentonite, gelatine, tragacanth, polyvinylpyrrolidone or polyvinyl alcohol. It is also possible to use lipophilic gel bases or microemulsions.

Dusting powders contain pulverulent additives, such as starch, stearate, silicon dioxide, clay, magnesium carbonate, talc, cellulose, zinc oxide and, in particular, lactose.

Stabilizers, antioxidants, preservatives, humectants, regreasing agents, solvents or auxiliaries can be added to all the formulations to improve the penetration and efficacy.

Examples of agents which improve penetration are propylene glycol, polyethylene glycol, dimethylsulphoxide, decylmethylsulphoxide, azones, N-methylpyrrolidone, diethyltoluamide, ethanol, isopropyl myristate, isopropyl palmitate, oleic acid and its esters, medium-chain triglycerides, dimethyl isosorbitol, 2-octyldodecanol, branched fatty acids, benzyl alcohol, urea, salicylates and surfactants.

B. Adhesive topical formulations

Where animals are treated, it has proved advantageous to use adhesive topically applicable formulations and the implement the invention as illustrated by way of example below.

Topical formulations according to the invention which can be applied to both wet and dry animals are characterized, for example, in that they contain ($a^1$) 0.1–20%, preferably 0.1–5%, of an active compound of the formula I, ($a^2$) 0.01 to 10% of a corticosteroid, (b) 1–40%, preferably 1–20%, of a water-soluble gel-or lacquer-forming polymer, (c) 40–98%, preferably 60–90%, of an organic water-miscible solvent which evaporates faster than water and in which the polymer does not dissolve, and (d) 0.1–10% of various additives, for example plasticizers, suspending auxiliaries, antioxidants, spreading agents, dyestuffs and the like.

To prepare the formulations, polymers which are known per se or salts thereof are suspended in a solvent in which they are not soluble. On the other hand, the polymers swell in water to form a gel. The active compound is either suspended or dissolved in the solvent. The solvent must be water-miscible and be able to evaporate faster than water. The customary formulation auxiliaries can be added to the suspension in order to guarantee a suspension which can easily be shaken up or is homogeneous. It may also be desirable to add a plasticizer so that the film which forms is later kept elastic.

If such a suspension is poured or sprayed onto a wet animal, as the solvent evaporates the polymer swells to form a gel which dries out to a lacquer or film layer and thereby incorporates the active compound. This layer remains stuck to the coat of hair or skin for a long time and is washed off only slowly - gradually - by showers of rain or a dipping bath.

The suspension is diluted with water in approximately equal proportions. It then still has a low viscosity and the polymer has not yet swollen, so that it can be applied effortlessly with the usual equipment. Here also, a gel and later a film forms after the solvent has evaporated, as already described above.

Possible gel- and film-forming agents are all the macromolecular compounds which do not dissolve in the water-miscible organic solvent and, after mixing with water, swell to form a gel which gives a type of film after drying.

Following a classification of macromolecular auxiliaries such as is described, for example, by Keipert et al. in Die Pharmazie 28, 145-183 (1973), above all ionic macromolecules in their salt form are used. These are, inter alia, sodium carboxymethylcellulose, polyacrylic acid, polymethacrylic acid and salts thereof, sodium amylopectin semiglycolate, alginic acid and propylene glycol alginate as the sodium salt, gum arabic, xanthan gum and guar gum.

Amphoteric macromolecules, such as protein derivatives, for example gelatine, are just as suitable as non-ionic polymers, for example methylcellulose, other cellulose derivatives and soluble starches, which meet the above requirements.

Suitable solvents are all the water-miscible liquids which do not dissolve the macromolecule and evaporate faster than water.

Examples of possible solvents are alkanols, such as ethanol and isopropyl alcoholk ketones, such as acetone and methyl ethyl ketone, and glycol ethers, such as ethylene glycol monomethyl ether or monoethyl ether.

One or more solvents can be used in the preparation of the formulations according to the invention of the type described above.

Other auxiliaries which are suitable for such formulations are:

(a) Substances which can stabilize the suspension, for example colloidal silicic acid, montmorillonites and the like, (b) Surfactants (including emulsifiers and wetting agents), for example
  1. anionic surfactants, such as Na lauryl-sulphate, fatty alcohol ether-sulphates and mono/dialkyl polyglycol ether-orthophosphoric acid ester monoethanolamine salts;
  2. cationic surfactants, such as cetyltrimethylammonium chloride;
  3. amophlytic surfactants, such as di-Na N-lauryl-B-iminodipropionate or lecithin; and
  4. non-ionic surfactants, for example polyoxyethylated castor oil, polyoxyethylated sorbitan monooleate, sorbitan monostearate, cetyl alcohol, glycerol monostearate, polyoxyethylene stearate and alkylphenol polyglycol ethers, (c) Stabilizers for preventing the chemical degradation which occurs with some active compounds, such as antioxidants, for example tocopherols and butylhydroxyanisole, and (d) Plasticizers for the elasticity of the film-forming agents, for example glycerol and propylene glycol.

All the formulations customary in dermatology and cosmetics are preferably suitable as use forms for application of the topical formulations according to the invention for combating bacterial diseases in humans. Formulations which may be mentioned in particular are those which, after application to the skin, are not immediately washed off on contact with water, that is to say those which contain film-forming or water-repellent additives, such as the formulations already mentioned above. Formulations of this type are, for example, solutions, sprays, lotions and ointments (here both emulsion ointments and suspension ointments and sticks analogous to insect repellant sticks).

C. Liquid formulations with spreading agents

Spreading oils can also be added to the formulations according to the invention, if these are in liquid form, for better distribution on surfaces, in particular on the skin.

Spreading oils are understood as those oily liquids which are distributed particularly easily on the skin. They are known as such in cosmetics. According to a proposal by R. Reymer, Pharm. Ind. 32, 577 (1970), they can be characterized, for example, by their surface tension in respect of air, which should accordingly be less than 30 dynes/cm.

The following substances are particularly suitable spreading agents:

Silicone oil of varying viscosity

Fatty acid esters, such as ethyl stearate, di-n-butyl adipate, hexyl laurate and dipropylene glycol pelargonate, esters of a branched fatty acid of medium chain length with saturated $C_{16}$-$C_{18}$ fatty alcohols, isopropyl myristate, isopropyl palmitate, caprylic/capric acid esters of saturated fatty alcohols of $C_{12}$-$C_{18}$ chain length, isopropyl stearate, oleyl oleate, decyl oleate, ethyl oleate, ethyl lactate, waxy fatty acid esters, such as synthetic duck uropygial gland fat, dibutyl phthalate, diisopropyl adipate, ester mixtures related to the latter and the like.

Triglycerides, such as caprylic/capric acid triglyceride, triglyceride mixtures with vegetable fatty acids of $C_8$-$C_{12}$ chain length or other specifically selected naturally occurring fatty acids, partial glyceride mixtures of saturated and unsaturated fatty acids which optionally also contain hydroxyl groups, monodiglycerides of the $C_8$/$C_{10}$-fatty acids and others.

Fatty alcohols, such as isotridecyl alcohol, 2-octyldodecanol, cetylstearyl alcohol and oleyl alcohol.

Fatty acids, such as oleic acid.

Particularly suitable spreading oils are the following: isopropyl myristate, isopropyl palmitate, caprylic/capric acid esters of saturated fatty alcohols of $C_{18}$-$C_{18}$ chain length and waxy fatty acid esters, such as synthetic duck uropygial gland fat.

D. Plasters

Other topically applicable formulations of the present invention are medicinal plasters for release of the active compounds of the formula I to the skin over a prolonged period of time.

The invention accordingly also relates to medicinal plasters for administration of an active compound of the formula I to the skin, which contain a top layer consisting of a longitudinally-transversely elastic, preferably textile sheet-like structure, in particular a knitted fabric or mesh fabric, impregnated or coated with a polymer, a reservoir layer and a pull-off protective layer, the reservoir layer containing a polymer consisting of polyisobutylene and/or copolymers thereof, an entraining agent and a resin.

Polymers in the sense of this section of the invention are preferably understood as polyisobutylene and/or copolymers thereof.

Polyisobutylenes in the sense of the invention are understood as polyisobutylenes which, due to their preparation, have a molecular weight distribution $M_w/M_N$ of 1.5 to 3.5, preferably 2.0 to 3.0, and a viscosity-average molecular weight—again as a result of their preparation—of 30,000 to 4,000,000 g/mol. The viscosity-average molecular weight of the polyisobutylenes to be employed according to the invention is preferably 50,000 to 1,000,000 g/mol, particularly preferably 80,000 to 500,000 g/mol. The viscosity-average molecular weight can be determined in a known manner as described in the Polymer Handbook, J. Brandrup and F. H. Immergut, Wiley & Sons, N.Y., 1975, Chapter IV, page 35.

These polyisobutylenes have been known for a long time and can be prepared, for example, according to U.S. Patent No. 2,203,873 or according to German Patent No. 704,038 with acid catalysts.

Copolymers of isobutylene in the sense of the invention are those of isobutylene with 0.5 to 5 mol % of conjugated diolefins, preferably those with 4 to 6 C atoms, such as, for example, buta-1,3-diene, piperylene and 2,3-dimethylbutadiene, and particularly preferably with isoprene, the molecular weights of which can be 30,000 to 200,000 g/mol. These isobutene copolymers are also known. Polyisobutylene homopolymers with a viscosity-average molecular weight of 80,000 to 500,000 are particularly preferably employed.

Entraining agents in the context of the invention are to be understood as oils, fatty acid esters, triglycerides, alcohols and/or fatty acids.

Oils in the sense of that part of the invention concerning medicinal plasters are to be understood as high-boiling aliphatic, araliphatic and/or aromatic hydrocarbons, preferably paraffin oil, purcellin oil, perhydrosqualene and solutions of microcrystalline waxes in oils, and mineral oils, preferably oils with a boiling range of between 150° C. and 400° C.; and furthermore unsaturated hydrocarbons with at least 16 C atoms, such as, for example, oligomers of monoolefins, such as tetraisobutylene, pentaisobutylene or hexaisobutylene, or liquid polymers of diene(monoene) (co)polymers. Examples of liquid polymers of conjugated dienes are those of butadiene, isoprene, 1,3-pentadiene and 2,3-dimethylbutadiene, copolymers of various dienes and liquid copolymers of a conjugated diolefin and small amounts of monoolefines, such as, for example, but-1-ene, isobutene, hex-1-ene, oct-1-ene or styrene, with a molecular weight of 400 to 6,000, preferably 800 to 3,000, iodine numbers of 200 to 500 and viscosities of 100 to 10,000 cP at 50° C.

Liquid polybutadiene polymers which are at least 90% 1,4-linked and have a content of cis double bonds of more than 60% and molecular weights of 1,000 to 4,000 are particularly preferred.

Oils are also understood as being silicone oils of varying viscosity, preferably with average molecular weights of 312 to 15,000, particularly preferably polydimethylsiloxanes.

Fatty acid esters are to be understood as those which contain at least 12 C atoms, preferably 15 to 46 C atoms and particularly preferably 16 to 36 C atoms.

Amongst these, there are to be understood in particular: ethyl stearate, hexyl laurate, dipropylene glycol pelargonate, cetyl palmitate, isopropyl myristate, isopropyl palmitate, carpylic/capric acid esters of saturated fatty alcohols of $C_{12}$–$C_{18}$ chain length, isopropyl stearate, oleyl oleate, decyl oleate and synthetic duck uropygial gland fat, and in particular in each case individually or as a mixture.

Triglycerides are understood as being pure or mixed esters of glycerol with fatty acids of $C_8$–$C_{18}$ chain length, preferably caprylic and/or capric acid triglycerides.

Fatty acids are understood as being saturated or unsaturated fatty acids, preferably those with 12 to 24 C atoms, individually or as mixtures with one another, and particularly preferably oleic acid.

Oils in the sense of the invention are furthermore understood as being: sweet almond oil, avocado oil, sesame oil, castor oil, olive oil, grapeseed oil, clove oil, groundnut oil, corn oil, hazelnut oil, jojoba oil, carthamus oil and wheatgerm oil, in each case individually or as a mixture.

Resins in the sense of that part of the invention which affects plasters are understood as being rosin, dehydrogenated rosin, glycerol esters of dehydrogenated rosin, glycerol esters of rosin gum, hydrogenated rosin, glycerol esters of hydrogenated rosin, pentaerythritol esters of hydrogenated rosin, methyl esters of hydrogenated rosin, polymerized rosin, glycerol esters of polymerized rosin, terpene resins, coumarone/indene resins, hydrygenated petroleum resins, such as maleic anhydridemodified rosin and rosin derivatives, $C_5$-petroleum resins and half-esters of styrene/maleic acid copolymers, individually or as in a mixture with one another. Polyterpene resins of alpha- or beta-pinene or modified glycerol esters of rosin are particularly preferred. Depending on the properties required in respect of tackiness and adhesion to the area to which the resulting plaster is to be applied, these resins can be used either by themselves or in combination with one another.

The active compounds of the formula 2 can be incorporated into the reservoir layer in the plasters of the invention in an amount of 1 to 30% by weight, preferably 2 to 20% by weight. The percentages by weight relate to the total reservoir.

Active substances or cooling or fragrant substances, preferably methyl salicylate, glygol salicylate, salicylic acid, menthol, peppermint oil, camphor, thymol, acrinol, scopolia extract, chlorpheniramine maleate, benzyl nicotinate, capsicum extract, nonylvanillylamine and capsaicin, can additionally also be added to the active substances of the formula I.

If necessary, additives and fillers, for example antiageing agents, antioxidants and reinforcing fillers, can be added to the plasters according to the invention.

Longitudinally and transversely elastic knitted fabrics and mesh fabrics have been used as the covering layer for the plasters according to the invention (see, for example, Koch-Satlow, Grosses Textillexikon (Large Textile Encyclopaedia), Deutsche Verlagsanstalt Stuttgart 1965).

Knitted fabrics and mesh fabrics are accordingly textile sheet-like structures which are produced from one or more thread systems on knitting machines by forming stitches. A distinction is made between two categories: weft knitted and mesh fabric (main feature: threads run in the transverse direction, analogous to the filling direction of woven fabrics) and warp knitted fabric (main feature: threads run in the longitudinal direction, analogous to the warp direction of woven fabrics).

The separation of terms into knitted fabric and mesh fabric usual in specialist terminology relates to the production process. In knitting, the stitches of one row of stitches are formed (sloughed) at the same time, whereas in meshing one stitch is formed after the other. However, there are exceptions to the assignment of the terms. From the point of view of binding, there is no difference between weft knitted fabrics and mesh fabrics.

In contrast to woven fabrics, knitted fabrics and to woven fabrics, knitted fabrics and mesh fabrics have a high extension and elasticity, especially in the transverse direction; moreover, because of the stitch structure, they have a large pore volume, which promotes permeability to air and thermal insulation. These and other properties can be varied substantially by their formation and also by the choice of fibre and yarn.

The knitted fabrics and mesh fabrics used according to the invention preferably have a stretch character. The customary methods of textile technology are used to achieve this stretch character (see Koch-Satlow, page 441), or elastomer fibres or elastomer yarns are used directly when choosing the base materials for the knitted fabric and mesh fabric.

As well as knitted fabrics and mesh fabrics, textile sheet-like structures with a stretch character can in general be used as the covering layer for the plasters according to the invention, that is to say all three-dimensional structures of natural and synthetic textile fibers, such as plaited materials, non-wovens or felts, are suitable as the top layer.

Base materials which can be used for the top layer are, inter alia, fibers and filaments of polyamide, polyester, polyurethane, polyamide-polyurethane, cotton, viscose staple and animal wool.

The textile top layer of the plasters according to the invention is impregnated or coated. The customary techniques and materials are used for coating and impregnation (see also Koch-Satlow, pages 157 to 159 and page 616 et seq.).

The top layer is preferably impregnated or coated with polyisobutylene. The molecular weight of the polyisobutylene here is preferably <1,000,000 g/mol (viscosity-average).

Preferred possible coating and impregnating materials are the polyisobutylenes which are also contained in the reservoir layer, but they have higher molecular weights and are not tacky.

The pull-off film of the plasters according to the invention can consist of occlusive, flexible or non-flexible materials, such as polyethylene, polypropylene, polyethylene, terephthalate, nylon and other known films. Metal foils, such as aluminum foil, by themselves or laminated with polymers, can also be used as the pull-off film. Multi-layer films, such as laminates of polyethylene with polyester PE terephthalate and vapor-deposited with aluminum, can also be used. Other pull-off films are, inter alia, polyesters treated with silicone, polyethylene terephthalate with terminal silicone groups, treated paper, silicone-treated paper, paper coated with polyethylene and the like.

E. Gels

The invention preferably also relates to topically applicable formulations in the form of gels. Gels here are understood as being disperse "solid/liquid" systems in which the disperse phase is no longer freely mobile.

Topical formulations of the active compounds of the formula I which are in the form of gels are suitable for the treatment of bacterial infections of, preferably, body cavities, in particular the oral cavity. The depot action, good adhesion properties and higher bioavailability of the active substances permit short-term therapy.

In order to shorten the duration of the therapy, a certain depot action and a higher bioavailability of the active compounds is required. The formulations according to the invention in gel form are particularly suitable for this. If a shortening in the duration of therapy is to be achieved without a further increase in the active compound concentration, optimum bioavailability of the active substance must be ensured.

In the region of the oral mucosa in particular, formulations which on the one hand have an adequate adhesion after application to the oral mucosa and on the other hand can release a sufficient amount of the active compound contained in the formulation, even in solution in the saliva, are therefore required.

It has been found that those formulations of the active compounds of the formula I in combination with corticosteriods which contain a cellulose ether, in particular hydroxypropylcellulose, sodium alginate or propylene glygol alginate as the gel-forming agent and in addition the customary formulation auxiliaries facilitate optimum adhesion properties and optimum release of the active compound and therefore a shortened duration of therapy by achieving antibacterial concentrations of the active compound. This effect is achieved by the bioavailability if the active compounds contained in the formulations being increased by adhesive properties, so that the release of active compound in the saliva can be increased.

Active compounds which can be formulated in this manner are all the active compounds of the formula I, in particular ciprofloxacin and the other active compounds mentioned on page 3. They are preferably present in the gels according to the invention in amounts of 0.05 to 30% by weight, preferably 0.05 to 0.5% by weight and in particular 0.1 to 1% by weight. The amounts of cortisteriod correspond to the amounts stated above.

Possible gel-forming agents are those macromolecular compounds which can dissolve or swell both in water and in organic solvents. Cellulose ethers may be mentioned above all here, and 2.5 to 17.5% of these are required.

Following a classification of the macromolecular auxiliaries (Keipert et al., Die Pharmazie 28, 145–183 (1973)), above all ionic macromolecules in salt form are used. These are, inter alia, sodium carboxymethylcellulose, polyacrylic acid, polymethacrylic acid and salts thereof, sodium amylopectinsemiglycolate, alginic acid and propylene glygol alginate as the sodium salt, gum arabic and guar gum.

Amphoteric macromolecules, such as protein derivatives, for example gelatine, are just as suitable as non-ionic polymers, for example methylcellulose, hydroxypropylcellulose and soluble starches, which meet the above requirements.

Possible gel-forming agents, which also have a stabilizing action, are long-chain linear high molecular weight polysaccharides with a molecular weight of more than one million. 0.1 to 1.5% of such stabilizers is required.

Suitable solvents are water and also all water-miscible solvents. Examples of possible solvents are alkanols, such as ethanol and isopropyl alcohol, benzyl alcohol, propylene glycol and the like.

Those macromolecular compounds such as, for example, hydroxypropylcellulose (probable molecular weight 2,000,000) have been found to be particularly stable gel combination bases.

The gels according to the invention preferably contain 2.5 to 35.0% by weight of the spreading agents mentioned under C.

F. Dusting powders

Topically applicable formulations according to the invention in dusting powder form contain the active compounds of the formula I and corticosteroids, and preferably dusting powder bases, such as rice starch, corn starch, wheat starch, talc, Bolus alba and Bolus rubra, kieselguhr, Aerosil, magnesium oxide, magnesium carbonate, zinc oxide and titanium dioxide.

The following dusting powder raw materials can in general be used according to the invention: Aerosil, aluminum hydroxide, palmitate and stearate, amylum non mucilaginosum, arrowroot, Avicel microcrystalline cellulose, barium sulphate, bolus, Cab-o-sil, calamine, calcium carbonicum praecipitatum, calcium silicate, stearate and sulphate, Calflo, dextrans, ekasil, flosilite, Glaxie Micron, gasil, kaolin, kieselguhr, silicic acid D 17, kirusol, Kronos titanium dioxide pigments, laminarin, luvokoll, magnesium carbonate, oxide, silicate, stearate and trisilicate, magnesol, marinco, metallic soaps, metasap, lactose, NAL, neosyl, oracid powder, ottalume, polyethylene, polyamide powder, polyester powder, Pontybond 2150, Powdertrol, Quso, rice starch, Santocel C, Sea sorb, soap fibroin, Sicol, Siflox, silica gel, Silin S 100, S-Micron Silica, Syloid, Talcum cetylatum, talc, Tego metallic soaps, Tiotal, Tioxide, titanium dioxide, titanium stearate, Veegum, Vinylon, Witcarb and zinc carbonate, myristate, oxide and stearate.

Starch, in particular rice starch and wheat starch, are preferably used as the dusting powder base for the active compounds of the formula I and the corticosteroids. Etherified starches are also preferably used.

Dusting powders which contain the active compounds are prepared with solid active compounds of the formula I and the corticosteroids by mixing the active compounds in finely divided form with the corresponding amount of dusting powder base from the point of view of mixing of powders.

They can also be introduced into aerosol compressed gas packs together with liquefied propellants and used as sprayable dusting powders. For these, about 8 to 9 parts by weight of propellant are to be used per part of dusting powder.

Liquid or semi-solid active compounds of the formula I and the corticosteroids are triturated intimately with a small amount of the base and the composition, which is then dried, is mixed with the remainder of the dusting powder base. If appropriate, volatile solvents can also be employed as auxiliaries so that the active compounds are absorbed uniformly onto the dusting powder base.

G. Suspensions

Suspensions according to the invention contain the active compounds of the formula I and the corticosteroids in solid form, dispersed in a liquid phase. The particle size of the dispersed active compounds is within the limits of 0.1 μm to about 100 μm. Depending on the use, the solids content in a suspension according to the invention is between about 0.5% and 40%. Their fundamental property is said to be the slow sedimentation of the solid particles and the ease with which they can be shaken up, in order to avoid incorrect dosages.

Suspensions according to the invention are as a rule prepared by triturating the solid with a small amount of liquid and gradually diluting the mixture to the final volume. If the dispersing agent consists of several liquids (for example Mucilago Tylose, glycerol and water), the component with the highest viscosity is used for the trituration. The final mixture can be homogenized mechanically with the aid of mixers, homogenizers, corundum disc mills, bead mills, ultrasound and the like.

The following measures are taken to prepare stable suspensions according to the invention:

Increase in the wettability of the particles and controlled flocculation by addition of amphiphilic auxiliaries and suitable electrolytes.

Increase in the viscosity of the dispersing agent to reduce the rate of sedimentation.

As with emulsions, surfactants can be used to reduce the solid/liquid surface tension.

These are absorbed by the hydrophobic particles of the disperse phase so that their solvated hydropholic molecular portions project away from the active compound into the dispersing agent. If ionic surfactants are used, the particles are also given a sufficient electrostatic charge, as well as being wetted well, which helps to stabilize the suspension.

Electrolytes such as phosphates, alkali metal carbonates, citrates, gallates and the like which determine the potential after adsorption onto the active compound particles lead to a high Zeta potential and thus have the effect of mutual repulsion.

Suspensions which can easily be shaken up again and can therefore be dosed uniformly can be prepared by means of the active compounds of the formula I and the corticosteroids by flocculating the originally hydrophobic particles initially negatively charged by an anionic surfactant by means of a calcium salt or aluminium salt. The loose, bulky sediment which forms can easily be redispersed by shaking.

The addition of macromolecular substances, such as methylcellulose, starch, tragacanth and the like has the effect of building up sorbate shells around the particles of the disperse phase, in addition to increasing the viscosity. This build-up of sorbate shells in turn impedes aggregation.

Gel-forming agents which impart thixotropic properties to the external phase are particularly effective. The gel structure formed in the resting state prevents sedimentation of the disperse phase. Under the action of weak shearing forces (shaking), the dispersion agent becomes free-flowing and the suspension can be easily dosed.

The statements made on aqueous suspensions also apply vice versa for oily suspensions. Surfactants, for example, of the metallic soap type are indicated here, above all for processing oxophilic (hydrophilic) solids. However, the content of free fatty acids in the oil or a corresponding addition is frequently already sufficient for lyophilization of zinc oxide or other hydrophilic substances used in medicaments. The effect of an additive with such a wetting action can already be seen in the appearance, for example of a zinc oil: while zinc oxide which has not been wetted sediments cumulatively and gives a glossy supernatant of pure oil (above all when liquid paraffin is used), ZnO particles wetted with the aid of fatty acids form flocks, sediment little and impart a matt appearance to the surface.

H. Emulsions

The topical formulation, according to the invention, of the active compounds of the formula I and the corticosteroids can also be in the form of "liquid/liquid" disperse systems.

According to "Arzneiformenlehre" ("Drug form doctrine"), P. H. List, Wissenschaftliche Verlagsgesellschaft mbH, Stuttgart 1985, page 168, the following points should be taken into consideration for preparation of emulsions:

| | |
|---|---|
| 1. Type of emulsion required | oil-in-water, water-in-oil, bicoherent system |
| 2. Viscosity | flowable or spreadable system |
| 3. Temperature stability | stability in the widest possible temperature range, sterilizability |
| 4. Degree of division | droplet size > 1 μm for the usual emulsions |
| 5. Constituents | choice of components for therapeutic, physiological, technological and economic reasons |
| 6. Concentration ratios | for application technology reasons |
| 7. Equipment and batch sizes | |

Because of the large number of factors, it is not possible to draw up generally applicable preparation rules. Rather, series of experiments should be carried out, and for these the HLB system, the Lin process for preparation of oil-in-water emulsion, the plotting of three-component graphs or the formation of emulsifier gels may be helpful.

Emulsifiers and other auxiliaries for the preparation of topical formulations according to the invention are described in H. P. Fiedler, Lexikon der Hilfsstoffe für Pharmazie, Kosmetik und angrenzende Gebiete (Encyclopaedia of Auxiliaries for Pharmacy, Cosmetics and Related Fields), Editio Cantor K. G., Aulendorf i. Württ., 1971, in particular on pages 185–194.

Emulsions of the active compounds of the formula I in combination with the corticosteroids can be used externally. Both types of emulsion, that is to say oil-in-water and water-in-oil emulsions, can be used externally.

Liquid oil-in-water emulsion, which are often also called lotions, are used chiefly for dermatological purposes. The semi-solid forms are called washable ointments; as are the semi-solid water-in-oil emulsions called creams. Liquid water-in-oil emulsions for external use have also been given in DAB 6 under the name liniments.

I. Solutions

The topically applicable formulations, according to the invention, of the active compounds of the formula I and the corticosteroids include solutions.

The choice of a solvent or solvent mixture for the preparation of the formulations according to the invention depends primarily on the nature of the substance or substance mixture to be dissolved. Moreover, however, the question of whether all or some of the solvent remains in the finished formulation plays a role. In the case where it remains, the solvent must above all be physiologically acceptable.

For these reasons, only a relatively small number of liquids are suitable solvents for medicament preparation.

That used by far the most frequently is water.

Suitable solvents are therefore water and all water-miscible solvents. Possible solvents are, for example, alcohols, such as ethanol, isopropyl alcohol and propylene glycol, polyethylene glycols, glycerol, methylcellosolve, cellosolve, esters, morpholines, dioxane, dimethylsulphoxide and the like.

One or more solvents can be used to prepare the formulations according to the invention. Suitable solubilizing agents are, above all: surfactants, such as polyoxyethylated sorbitan fatty acid esters, polyoxyethylated fatty acid ethers and esters, and the like. Water-immiscible solvents are moreover also suitable, such as liquid esters and oils, in particular isopropyl myristate, isopropyl palmitate, 2-octyldodecanol, medium-chain triglycerides, adipic acid esters, sebacic acid esters, paraffin oil and silicone oil, and mixtures thereof, as well as water-miscible solvents and surfactants.

J. Ointments, pastes, creams, foams (According to Ullmann, Volume 18, Pharmazeutische Technologie und Arzneiformenlehre (Pharmaceutical Technology and Drug Form Doctrine), P. H. List, 4th edition, Wissenschaftl. Verlagsgesellschaft mbH, Stuttgart).

Ointments are gels with a plastic deformability which can contain dissolved emulsified or suspended active compounds of the formula I and corticosteroids.

They are used for local treatment of diseased parts of the skin or mucous membrane. They can also fulfil the function of protecting and covering ointments here. If the ointments contain active compounds of the formula I and corticosteroids which pass into and penetrate the deeper-lying layers of skin and act there, they are called penetration ointments. Ointments in which the active compounds pass into the underskin tissue and finally into the blood circulation are called absorption ointments (percutaneous or transcutaneous absorption).

Ointments are called by different names, depending on their composition, their consistency or the site of application:

Unguents, ointments (French: pommades) is either the generic term for this medicament form or means anhydrous formulations based on various bases.

Cerates is the name for ointments which consist of a mixture of wax and oil.

Cremors and creams are ointments with a particularly soft consistency containing relatively large amounts of water.

Glycerols are glycerol-containing formulations with a semi-solid consistency.

Pastae and pastes are ointments with a high content of pulverulent solids and therefore a high consistency.

Oculents, ophthalmic unguents and eye ointments are soft ointments for application into the conjunctival sac and to the edges of the lids, on which particular requirements in respect of purity and particle size are imposed.

Ointments bases which are used for the topically applicable formulations of the invention are hydrocarbon gels, lipogels, hydrogels, polyethylene glycol gels and silicone gels.

Vaseline, Plastibase, waxes (according to the DGF), in particular beeswax, spermaceti DAB 8, cetaceum, woolwax DAB 8. Lanae Cera, oleyl oleate DAB 8. Oleyli oleas, isopropyl myristate, lard, hardened groundnut oil, glycerol, sorbitol solutions, low molecular weight polyethylene glycols, colloidal silicic acid, Aerosil, swellable clays, such as bentonite, potash soap, soft soap, Opodeldoc, starch, cellulose derivatives, polyacrylic acid, polyethylene glycol gels DAB 8 and silicone oils are preferably suitable.

The topical formulations according to the invention are used in ointment form as solution ointments, emulsion ointments and suspension ointments. They preferably contain antioxidants, such as avenol, avenex, conidendrin, norconidendrin, nordihydroguajaritic acid, tocopherol, ascorbic acid esters, for example the stearate, palmitate, myristate and laurate, 3-butyl-4-hydroxyanisole, hydroquinone, propyl gallate, citric acid, cis-methylmaleic acid, gallic acid esters, such as ethyl gallate and propyl gallate, Ionol, BHT and tetraoxydimethylbisphenyl (TDBP).

Pastes are highly concentrated suspensions with a flow limit for use on the skin or mucous membrane. They contain a large amount of insoluble powder dispersed in a liquid or ointment-like vehicle.

The pulverulent constituents with a particle size of not more than 100 μm are gradually triturated with the dispersing agent, which if necessary is melted or softened on a waterbath, to give a uniform composition, which is homogenized to the highest possible degree with an ointment mill.

Creams in the sense of the invention are particularly smooth formulations which contain relatively large amounts of water in the form of oil-in-water or water-in-oil emulsions. The ratio of the aqueous to the oily phase determines the viscosity and the ease of spreading of a cream. Suitable bases, depending on the type of emulsion, are, for example, various grades of Lanette (sodium fatty alcohol sulphate), cetylstearyl alcohol or wool fat, woolwax alcohols and the like.

The topical formulations according to the invention can also be in the form of foams. Foams here are understood as being disperse "gaseous/liquid" systems (for the definitions, terms and preparation see "Arzneiformenlehre" ("Drug Forms Doctrine"), List).

The topical formulations according to the invention exhibit a broad antibacterial spectrum against Gram-positive and Gram-negative germs, in particular against Enterobacteriaceae, and anti-inflammatory properties; above all also against those germs which are resistant to various antibiotics, such as, for example, penicillins, cephalosporins, aminoglycosides, sulphonamides and tetracyclines, coupled with a low toxicity.

The formulations according to the invention are active against a very broad spectrum of microorganisms. With their aid, Gram-negative and Gram-positive bacteria and bacteria-like microorganisms can be combated and the diseases caused by these pathogens can be prevented, alleviated and/or cured.

The topical formulations according to the invention are particularly active against bacteria and bacteria-like microorganisms and sensitive processes as well as other corticosteroid indications. They are therefore particularly suitable in human and animal medicine for the prophylaxis and chemotherapy of locak and, if appropriate, systemic infections caused by these pathogens.

For example, local and/or systemic diseases caused by the following pathogens or by mixtures of the following pathogens can be treated and/or prevented: Gram-positive cocci, for example Staphylococci (Staph. aureus and Staph. epidermidis) and Streptococci (Strept. agalactiae, Strept. faecalis, Strept. penumoniae and Strept. pyogenes); Gram-negative cocci (Neisseria genorrhoeae) and Gram-negative rod-shaped bacillae, such as Enterobacteriaceae, for example Escherichia coli, Haemophilus influenza, Citrobacter (Citrob. freundii and Citrob. divernis), Salmonella and Shigella; and furthermore Klebsiella (Klebs. pneumoniae and Klebs. oxytoca), Enterobacter (Ent. aerogenes and Ent. agglomerans), Hafnia, Serratia (Serr. marcescens), Proteus (Pr. mirabilis, Pr. rettgeri and Pr. vulgaris), Providencia and Yersinia, and the genus Acinetobacter. The antibacterial spectrum moreover includes the genus Pseudomonas (Ps. aeruginosa and Ps. maltophilia) and strictly anaerobic bacteria, such as, for example, Bacteroides fragilis, representatives of the genus Peptococcus, Peptostreptococcus and the genus Clostridium; and furthermore Mykoplasma (M. pneumoniae, M. hominis and M. urealyticum) and Mykobacteria, for example Mycobacterium tuberculosis.

The above list of pathogens is merely by way of example and is in no way to be interpreted as limiting. Examples which may be mentioned of diseases which can be caused by the pathogens or mixed infections mentioned and can be prevented, alleviated or cured by the topically applicable formulations according to the invention are: infectious diseases in humans, such as, for example, septic infections, bone and joint infections, skin infections, postoperative wound infections, abscesses, phlegmons, wound infections, infected burns, burn wounds, infections in the oral region, infections following dental operations, septic arthritis, mastitis, tonsillitis, genital infections and eye infections.

As well as in humans, bacterial infections can also be treated in other species. Examples which may be mentioned are: pigs: coli diarrhoea, enterotoxaemia, sepsis, dysentery, salmonellosis, metritis-mastitis-agalactiae syndrome and mastitis; ruminants (cattle, sheep, goats): diarrhoea, sepsis, bronchopneumonia, salmonellosis, pasteurellosis, mykoplasmosis and genital infections; horses: bronchopneumonia, joint ill, puerperal and post-puerperal infections and salmonellosis; dogs and cats: bronchopneumonia, diarrhoea, dermatitis, otitis, urinary tract infections and prostatitis; and poultry (chickens, turkeys, quail, pigeons, ornamental birds and others): mycoplasmosis, E. coli infections, chronic respiratory tract diseases, salmonellosis, pasteurellosis, psittacosis.

Bacterial infections in the breeding and husbandry of stock and ornamental fish can also be treated, the antibacterial spectrum being extended beyond the pathogens mentioned above to other pathogens, such as, for example, Pasteurella, Brucella, Campylobacter, Listeria, Erysiphelothrix, Corynebacteria, Borellia, Treponema, Nocardia, Rickettsia and Yersinia.

The present invention includes pharmaceutical formulations which, in addition to non-toxic, inert pharmaceutically suitable excipients, contain one or more compounds according to the invention or consist of one or more active compounds according to the invention, and to processes for the preparation of these formulations.

The present invention also includes pharmaceutical formulations in dosage units.

The abovementioned pharmaceutical formulations can also contain other pharmaceutically active compounds in addition to the compounds according to the invention.

The abovementioned pharmaceutical formulations are prepared in the customary manner by known methods, for example by mixing the active compound or compounds with the excipient or excipients.

EXAMPLES

Adhesive topical formulations

1. Example of a stick

Composition

| 1 | Ciprofloxacin hydrochloride × 1 H$_2$O | 0.2 g |
|---|---|---|
| 2 | Active compound X | 1.0 g |
| 3 | Beeswax | 12.0 g |
| 4 | Vaseline | 6.0 g |
| 5 | Cetyl alcohol | 4.0 g |
| 6 | Woolwax | 3.0 g |
| 7 | Isopropyl myristate | 9.0 g |
| 8 | Castor oil | 64.8 g |
| | | 100.0 g |

Preparation

Substances (3) to (8) are weighed and melted at about 70°, with stirring. Ciprofloxacin hydrochloride is suspended therein. The melt is poured into appropriate molds (sticks) and cooled to room temperature.

2. Example of a protective ointment

Composition

| 1 | Ciprofloxacin | 0.5 g |
|---|---|---|
| 2 | Active compound H | 0.5 g |
| 3 | Low molecular weight acrylic resin | 5.0 g |
| 4 | Demineralized water | 71.5 g |
| 5 | Ammonia | 1.0 g |
| 6 | Woolwax alcohol | 9.0 g |
| 7 | Tween 81$^R$ | 1.0 g |
| 8 | Liquid paraffin | 11.5 g |
| | | 100.0 g |

Preparation (a) Heat substances 1, 2, 6, 7 and 8 to 65° C., with stirring.
(b) Heat substances 3 and 4 (aqueous phase) to 65° C.
(c) Incorporate b into a, with vigorous stirring.
(d) Add the ammonia to c, with vigorous stirring, and cool to room temperature, with stirring.

3. Example of a film-forming concentrate

Composition

| 1 | Ciprofloxacin | 5.0 g |
|---|---|---|
| 2 | Active compound G$^1$ | 1.0 g |
| 3 | Sodium alginate | 9.0 g |
| 4 | Non-ionic emulsifier | 2.0 g |
| 5 | Colloidal silicic acid | 2.0 g |
| 6 | Isopropanol to 100 ml | 81.0 g |

| | | 100.0 g |
|---|---|---|

Preparation

Ciprofloxacin and hydrocortisone acetate are dispersed in 3 and 5, with stirring. 2 and 4 are introduced into the dispersion and the mixture is homogenized.

Before use, this suspension is shaken up and diluted 1+9 with water. A gel forms which, after drying, forms an elastic film on the skin and sticks for a relatively long time, even in contact with water.

4. Example of a solution

Composition

| 1 | Ciprofloxacin or norfloxacin + 0.5 g of active compound H | 0.03 g |
|---|---|---|
| 2 | Poly(methyl vinyl ether/monoalkyl maleate) | 2.5 g |
| 3 | Isopropanol | 96.97 g |
| | | 100.0 g |

Preparation

The solution can be applied to the skin. After drying, a film containing the active compounds is formed on the skin.

5. Example of a spray formulation

The solution from Example 4 is introduced into suitable aerosol cans with propane/butane as the propellant gas in a ratio of 1+2.

Plasters

Example 1

A 12.5% strength polyisobutylene solution (viscosity-average molecular weight 1,270,000) (in benzine) is applied to siliconized paper, a knitted fabric consisting of polyamide-polyurethane fibers is laminated on and the system is dried in a drying tunnel in zones at 70° / 90° / 100° C. (polymer 30 g/m$^2$).

A mixture consisting of 36,000 g of polyisobutylene of viscosity-average molecular weight 400,000, 44,928 g of light liquid paraffin, 9,000 g of polyterpene resin from β-pinene, 10,000 g of ciprofloxacin or ofloxacin or norfloxacin and 0.072 g of an antiageing agent, dissolved in benzine/acetone, is applied to siliconized paper and the paper is dried in a drying tunnel in zones at 70° / 90° / 100° C. (active compound release system about 150 g/m$^2$).

After drying, the polyisobutylene-impregnated knitted fabric with a stretch character is laminated on.

Example 2

A polymer solution (benzine/acetone) consisting of 36,000 g of polyisobutylene of viscosity-average molecular weight 1,270,000, 44.928 g of light liquid paraffin, 9.000 g of polyterpene resin from α-pinene, 5.000 g of ciprofloxacin and 5.000 g of active compound N and 0.072 g of anti-ageing agent was applied to siliconized paper and the paper was dried in a drying tunnel in zones at 70° / 90° / 100° C.

After drying, the active compound release system was laminated with polyisobutylene (as in Example 1) on coated stretch material.

The plasters according to the invention have just as good an absorption of the active compounds as conventional plasters coated with aluminum-polyethylene films.

The methods and materials described in Koch-Satlow, Grosses Textillexikon (Large Textile Encyclopaedia) are used, inter alia, for laminating the active compound depot onto the textile sheet-like structure with a stretch character.

Gels

Example 1

| | |
|---|---|
| Ciprofloxacin lactate | 0.20 g |
| Active compound prednisolone | 5.00 g |
| Benzyl alcohol | 3.00 g |
| Hydroxypropylcellulose | 2.50 g |
| (molecular weight 1,000,000) | |
| Demineralized water to | 100 g |

Example 2

| | |
|---|---|
| Ciprofloxacin acetate | 0.20 g |
| Hydrocortison acetate | 0.25 g |
| Benzyl alcohol | 3.00 g |
| Hydroxypropylcellulose | 2.5 g |
| (molecular weight 1,000,000) | |
| Demineralized water to | 100 g |

Example 3

| | |
|---|---|
| Norfloxacin hydrochloride | 0.20 g |
| Prednisolone | 5.00 g |
| Benzyl alcohol | 3.00 g |
| Hydroxypropylcellulose | 2.5 g |
| (molecular weight 1,000,000) | |
| Demineralized water to | 100 g |

Example 4

| | |
|---|---|
| Ofloxacin hydrochloride | 0.20 g |
| Prednisolone | 5.00 g |
| Benzyl alcohol | 3.00 g |
| Hydroxypropylcellulose | 17.50 g |
| (molecular weight 60,000) | |
| Demineralized water to | 100 g |

Creams

Example 1 oil-in-water cream

Phase I

| | |
|---|---|
| Sorbitan monostearate | 2.0 g |
| Polyoxyethylene (20) sorbitan monostearate | 1.5 g |
| Synthetic spermaceti | 3.0 g |
| Cetyl stearyl alcohol | 10.0 g |
| 2-Octyldodecanol | 13.5 g |

Heat to 75° C., stir and mix.
Phase II

| | |
|---|---|
| Ciprofloxacin, norfloxacin or | 1.0 g |
| ofloxacin, enoxacin, pefloxacin | | in combination with 1 to 2 g of active compounds A to Z and $A^1$ to $H^1$. Add to phase I, stir and suspend.
Phase III

| | |
|---|---|
| Benzyl alcohol | 1.0 g |
| Demineralized water | 68.0 g |

Heat to 75° C. and add to phase II. Mix intensively and cool slowly to room temperature, with further stirring. Homogenize.

Example 2 oil-in-water cream

Phase I

| | |
|---|---|
| Sorbitan monostearate | 1–3 g |
| Polyoxyethylene (20) sorbitan monostearate | 0.5–2.5 g |
| Synthetic spermaceti | 2–4 g |
| Cetyl stearyl alcohol | 5–15 g |
| Isopropyl myristate | 5–25 g |

Heat to 75° C., stir and mix.
Phase II

| | |
|---|---|
| Add ciprofloxacin, norfloxacin or ofloxacin | 0.5–1.5 g | and active active compounds A to Z or $A^1$ to $H^1$ in just such amounts to phase I, stir and suspend.
Phase III

| | |
|---|---|
| Benzyl alcohol | 0.5–1.5 g |
| Demineralized water | quant. sat. |

Heat to 75° C. and add to phase II. Mix intensively and cool slowly to room temperature, with further stirring. Homogenize.

Liquid plasters

Example 1

| | |
|---|---|
| Flupamesone | 1.0 g |
| Ciprofloxacin | 1.0 g |
| Benzyl alcohol | 5.0 g |
| Hydroxypropylcellulose | 10.0 g |
| (molecular weight 60,000) | |
| Isopropanol to | 100 ml |

Example 2

| | |
|---|---|
| Triamcinolone | 0.1 g |
| Ciprofloxacin | 0.1 g |
| Benzyl alcohol | 5.0 g |
| Isopropyl myristate | 6.0 g |
| Hydroxypropylcellulose | 10.0 g |
| (molecular weight 60,000) | |
| Isopropanol to | 100 ml |

Example 3

| Fluocinolone acetonide | 1.0 g |
|---|---|
| Ciprofloxacin | 1.0 g |
| Benzyl alcohol | 4.0 g |
| Isopropyl stearate | 10.0 g |
| Hydroxypropylcellulose (molecular weight 60,000) | 12.0 g |
| Isopropanol to | 100 ml |

Example 4

| Betamethasone valerate | 1.0 g |
|---|---|
| Ciprofloxacin | 1.0 g |
| 1,2-Propylene glycol | 1.0 g |
| Isopropyl myristate | 6.0 g |
| Hydroxypropylcellulose (molecular weight 60,000) | 10.0 g |
| Isopropanol to | 100 ml |

Example 5

| Norfloxacin | 0.1 g |
|---|---|
| Benzyl alcohol | 5.0 g |
| Isopropyl myristat | 6.0 g |
| Hydroxypropylcellulose (molecular weight 60,000) | 10.0 g |
| Isopropanol | to 100 ml |

Example 6

| Ofloxacin | 1.0 g |
|---|---|
| Benzyl alcohol | 5.0 g |
| Isopropyl myristate | 6.0 g |
| Hydroxypropylcellulose (molecular weight 60,000) | 10.0 g |
| Isopropanol | to 100 ml |

Example 7

| Prednisolone | 1.0 g |
|---|---|
| Ciprofloxacin | 1.0 g |
| Benzyl alcohol | 8.0 g |
| Isopropyl myristate/isopropyl stearate/isopropyl palmitate | 1.0 g |
| Hydroxypropylcellulose (molecular weight 60,000) | 10.0 g |
| Isopropanol | to 100 ml |

Example 8

| Prednisolone | 1.0 g |
|---|---|
| Norfloxacin | 1.0 g |
| Benzyl alcohol | 5.0 g |
| Isopropyl myristate | 6.0 g |
| Methylcellulose | 10.0 g |
| Isopropanol | to 100 ml |

Sprays

The active compound solutions or suspensions prepared according to Example 1 to 8 can also be processed to sprays. For this purpose, for example, a 60 to 90% active compound solution is mixed with 20 to 40% of the usual propellants, for example $N_2$, $N_2O$, $CO_2$, propane, butane, halogenohydrocarbons and the like.

Emulsions/Creams

Example 1 oil-in-water emulsion

Phase I

| "Glyceryl stearates" (mixture of mono- and diglycerides of palmitic and stearic acid) | 8.00 g |
|---|---|
| 2-Octyldodecanol | 10.00 g |
| Cetyl stearyl alcohol with about 12 mols of ethylene oxide | 1.50 g |
| Cetyl stearyl alcohol with about 30 mols of ethylene oxide | 1.50 g |
| Heavy liquid paraffin | 6.00 g |
| 1,2-Propylene glycol | 5.00 g |
| Caprylic/capric acid triglyceride | 6.00 g |

The mixture is stirred and melted at 70° C.

Phase II

| Demineralized water | 58.00 g |
|---|---|
| Phase III | 1.00 g |
| Prednisolone | 1.00 g |
| Ciprofloxacin suspended in benzyl alcohol | 3.00 g |

Phase II is heated to 75° C. and phase I, which has been heated to 70° C., is added, with stirring. The mixture is allowed to cool slowly to 40° C., phase III is added and the mixture is allowed to cool to room temperature, with stirring. The crude emulsion is homogenized at 20° to 25° C. in a high pressure homogenizer. Examples 2 and 3 are processed in an anlogous manner.

Example 2 oil-in-water emulsion

| Desoxycorticosterone | 5.00 g |
|---|---|
| Ciprofloxacin | 1.00 g |
| "Glyceryl stearates" mixture of mono- and diglycerides of palmitic and stearic acid | 8.00 g |
| Diglycerides of palmitic and stearic acid | 9.00 g |
| Cetyl stearyl alcohol with about 12 mols of ethylene oxide | 3.00 g |
| 2-Octyldodecanol | 10.00 g |
| Heavy liquid paraffin | 5.00 g |
| Benzyl alcohol | 5.00 g |
| Demineralized water | to 100 ml |

Example 3 oil-in-water emulsion

| Desoxycorticosterone | 5.00 g |
|---|---|
| Norfloxacin | 1.00 g |
| "Glyceryl stearates" mixture of mono- and diglycerides of palmitic and stearic acid | 9.00 g |
| Cetyl stearyl alcohol with about 12 mols of ethylene oxide | 3.00 g |
| 2-Octyldodecanol | 10.00 g |
| Benzyl alcohol | 5.00 g |
| Isopropyl myristate | 5.00 g |
| Demineralized water | to 100 ml |

Example 4 oil-in-water cream, soft consistency

| | |
|---|---|
| Prednisolone, fluocinolone acetonide, hydrocortisone acetate | 1.00 g |
| Ciprofloxacin, norfloxacin, ofloxacin | 1.00 g |
| "Glyceryl stearates" mixture of mono- and diglycerides of palmitic and stearic acid | 4.00 g |
| Cetyl palmitate | 4.00 g |
| Cetyl stearyl alcohol with about 12 mols of ethylene oxide | 1.00 g |
| Cetyl stearyl alcohol with about 30 mols of ethylene oxide | 1.00 g |
| Isopropyl myristate/isopropyl palmitate, isopropyl stearate mixture | 5.00 g |
| Weakly crosslinked polyacrylic acid of extremely high molecular weight | 0.50 g |
| 45% strength sodium hydroxide | 0.11 g |
| Glycerol | 3.00 g |
| Benzyl alcohol | 3.00 g |
| Demineralized water | to 100 ml |

Example 5 oil-in-water cream, soft consistency

| | |
|---|---|
| Active compounds A to Z or $A^1$ to $H^1$ in each case | 1.00 g |
| Ciprofloxacin, norfloxacin, ofloxacin | 1.00 g |
| "Glyceryl stearates" mixture of mono- and diglycerides of palmitic and stearic acid | 4.00 g |
| Cetyl palmitate | 4.00 g |
| Cetyl stearyl alcohol with about 12 mols of ethylene oxide | 1.00 g |
| Cetyl stearyl alcohol with about 30 mols of ethylene oxide | 1.00 g |
| Isopropyl myristate/isopropyl palmitate/ isopropyl stearate mixture | 5.00 g |
| Weakly crosslinked polyacrylic acid of extremely high molecular weight | 0.50 g |
| 45% strength sodium hydroxide | 0.11 g |
| Glycerol | 3.00 g |
| Benzyl alcohol | 3.00 g |
| Demineralized water | to 100 ml |

Example 6 oil-in-water cream, soft consistency

| | |
|---|---|
| Hyorocortisone acetate | 1.00 g |
| Norfloxacin, ofloxacin | 1.00 g |
| "Glyceryl stearates" mixture of mono- and diglycerides of palmitic and stearic acid | 4.00 g |
| Stearic acid | 4.00 g |
| Cetyl palmitate | 4.00 g |
| Cetyl stearyl alcohol with about 12 mols of ethylene oxide | 1.00 g |
| Cetyl stearyl alcohol with about 30 mols of ethylene oxide | 1.00 g |
| Isopropyl myristate/isopropyl palmitate/ isopropyl stearate mixture | 5.00 g |
| Weakly crosslinked polyacrylic acid of extremely high molecular weight | 0.50 g |
| 45% strength sodium hydroxide | 0.11 g |
| Glycerol | 3.00 g |
| Benzyl alcohol | 3.00 g |
| Demineralized water | to 100 ml |

Example 7 oil-in-water emulsion, non-greasy

Phase I

| | |
|---|---|
| Decyl oleate | 2.50 g |
| Isopropyl myristate | 2.50 g |
| Lihht liquid paraffin | 4.00 g |
| Polyethylene stearate | 0.90 g |
| Fatty acid esters of sorbitan and glycerol | 0.60 g |

The mixture is stirred and melted at 70° C. for 10 minutes.

Phase II

| | |
|---|---|
| Demineralized water | 50.00 g |
| Allantoin | 0.10 g |

Carbopol mucilage

| | |
|---|---|
| Denatured alcohol | 10.00 g |
| Carbopol 934 (weakly crosslinked polyacrylic acid) | 0.70 g |
| Demineralized water | 22.945 g |

The components are dispersed with a Turrax and the dispersion is left to swell for 2 hours and then neutralized with 0.155 g of 45% strength sodium hydroxide solution.

Phase II is heated to 75° C. and phase I, which has been heated to 70° C., is added, with stirring, and the mixture is cooled to 45° C.. Stir in the Carbopol mucilage at 45° C. and cool further to 40° C.. Add 1.00 g of collagen at 40° C. and cool to 25° C. Incorporate 1.0 g of ciprofloxacin into 3.0 g of benzyl alcohol and add to phase I and II.

The crude emulsion is then homogenized at 20° C. to 25° C. in a high pressure homogenizer, with stirring.

Examples 8, 9, 10 and 11 are processed in an analogous manner.

Example 8 oil-in-water emulsion, non-greasy

| | |
|---|---|
| Hydrocortisone acetate | 0.20 g |
| Ciprofloxacin | 0.10 g |
| Decyl oleate | 2.50 g |
| Isopropyl myristate | 2.50 g |
| Light liquid paraffin | 4.00 g |
| Polyethylene stearate | 0.90 g |
| Fatty acid esters of sorbitan and glycerol | 0.60 g |
| Allantoin | 0.155 g |
| Weakly crosslinked polyacrylic acid of extremely high molecular weight | 0.70 g |
| Collagen | 1.00 g |
| Benzyl alcohol | 3.00 g |
| Ethanol | 10.00 g |
| Demineralized water | to 100 ml |

Example 9 oil-in-water emulsion, non-greasy

| | |
|---|---|
| Hydrocortisone acetate | 0.15 g |
| Norfloxacin | 0.15 g |
| Decyl oleate | 2.50 g |
| Isopropyl myristate | 2.50 g |
| Light liquid paraffin | 4.00 g |
| Polyethylene stearate | 0.90 g |
| Fatty acid esters of sorbitan and glycerol | 0.60 g |
| Allantoin | 0.10 g |
| Weakly crosslinked polyacrylic acid of extremely high molecular weight | 0.70 g |

-continued

| | |
|---|---|
| 45% strength sodium hydroxide | 0.155 g |
| Collagen | 1.00 g |
| Benzyl alcohol | 3.00 g |
| Ethanol | 10.00 g |
| Demineralized water to | 100 ml |

Example 10 oil-in-water emulsion, non-greasy

| | |
|---|---|
| Hydrocortisone acetate | 0.10 g |
| Ofloxacin | 0.10 g |
| Decyl oleate | 2.50 g |
| Isopropyl myristate | 2.50 g |
| Light liquid paraffin | 4.00 g |
| Polyethylene stearate | 0.90 g |
| Fatty acid esters of sorbitan and glycerol | 0.60 g |
| Allantoin | 0.10 g |
| 45% strength sodium hydroxide | 0.155 g |
| Weakly crosslinked polyacrylic acid of extremely high molecular weight | 0.70 g |
| Collagen | 1.00 g |
| Benzyl alcohol | 3.00 g |
| Ethanol | 10.00 g |
| Perfume oil | 0.60 g |
| Demineralized water to | 100 ml |

Example 11 oil-in-water emulsion, non-greasy

| | |
|---|---|
| Hydrocortisone acetate, prednisolone in each case | 0.05 g |
| Ciprofloxacin | 0.05 g |
| Decyl oleate | 2.50 g |
| Isopropyl myristate | 2.50 g |
| Light liquid paraffin | 4.00 g |
| Polyethylene stearate | 0.90 g |
| Fatty acid esters of sorbitan and glycerol | 0.60 g |
| Allantoin | 0.10 g |
| 45% strength sodium hydroxide | 0.155 g |
| Weakly crosslinked polyacrylic acid of extremely high molecular weight | 0.70 g |
| Collagen | 1.00 g |
| Benzyl alcohol | 3.00 g |
| Ethanol | 10.00 g |
| Demineralized water to | 100 ml |

Example 12 oil-in-water emulsion, non-greasy

| | |
|---|---|
| Triamcinolone | 0.50 g |
| Ciprofloxacin | 0.10 g |
| "Glyceryl stearates" mixture of mono- and diglycerides of palmitic and stearic acid | 4.00 g |
| Cetyl palmitate | 4.00 g |
| Cetyl stearyl alcohol with about 12 mols of ethylene oxide | 1.00 g |
| Cetyl stearyl alcohol with about 30 mols of ethylene oxide | 1.00 g |
| Isopropyl myristate/isopropyl palmitate/isopropyl stearate mixture | 5.00 g |
| Weakly crosslinked polyacrylic acid of extremely high molecular weight | 0.50 g |
| 45% strength sodium hydroxide | 0.11 g |
| Glycerol | 3.00 g |
| Benzyl alcohol | 3.00 g |
| Demineralized water to | 100 ml |

Example 13 oil-in-water cream, soft consistency

| | |
|---|---|
| Flupamesone | 0.05 g |
| Ofloxacin | 0.05 g |
| "Glyceryl stearates" mixture of mono- and diglycerides of palmitic and stearic acid | 4.00 g |
| Cetyl palmitate | 4.00 g |
| Cetyl stearyl alcohol with about 12 mols of ethylene oxide | 1.00 g |
| Cetyl stearyl alcohol with about 30 mols of ethylene oxide | 1.00 g |
| Isopropyl myristate/isopropyl palmitate/isopropyl stearate mixture | 5.00 g |
| Weakly crosslinked polyacrylic acid of extremely high molecular weight | 0.50 g |
| 45% strength sodium hydroxide | 0.11 g |
| Glycerol | 3.00 g |
| Benzyl alcohol | 3.00 g |
| Demineralized water to | 100 ml |

Example 14 oil-in-water cream, soft consistency

| | |
|---|---|
| Prednisolone | 5.00 g |
| Norfloxacin, pefloxacin | 1.00 g |
| "Glyceryl stearates" mixture of mono- and diglycerides of palmitic and stearic acid | 4.00 g |
| Na stearate | 16.00 g |
| Cetyl stearyl alcohol with about 12 mols of ethylene oxide | 3.00 g 56 |
| Benzyl alcohol | 3.50 g |
| 2-Octyldodecanol | 2.50 g |
| Coconut fatty acid isopropyl ester (Isopropyl myristate/isopropyl palmitate, isopropyl stearate mixture) | 2.50 g |
| Light liquid paraffin | 3.00 g |
| Demineralized water to | 100 ml |

Gels

Example 1

Phase I
Dissolve

| | |
|---|---|
| Hydrocortisone acetate | 1.00 g |
| Ofloxacin | 1.00 g |
| in isopropanol | 40.00 g |
| subsequently stir in | |
| Polyol fatty acid ester | 4.00 g |
| Benzyl alcohol | 3.00 g |
| Diisopropyl adipate and dissolve. | 4.00 g |

Phase II
Introduce into

| | |
|---|---|
| demineralized water | 46.10 g |
| Carbopol 940 | 1.50 g |
| with stirring, allow to swell for about 2 hours and neutralize with | |
| 45% strength NaOH | 0.40 g. |

Incorporate phase I slowly in portions into phase II, with stirring.

Example 2

| | |
|---|---|
| Flupamesone | 1.00 g |

-continued

| | |
|---|---|
| Ciprofloxacin | 1.00 g |
| Polyol fatty acid ester | 4.00 g |
| Isopropyl myristate | 4.00 g |
| Benzyl alcohol | 1.00 g |
| Isopropanol | 45.00 g |
| Carbopol 940 | 1.50 g |
| 45% strength NaOH | 0.40 g |
| Demineralized water | 43.10 g |

Example 3

| | |
|---|---|
| Fluocinolone acetonide | 1.00 g |
| Ofloxacin | 1.00 g |
| Polyol fatty acid ester | 4.00 g |
| Coconut fatty acid isopropyl ester | 4.00 g |
| Benzyl alcohol | 5.00 g |
| Isopropanol | 45.00 g |
| Carbopol 940 | 1.50 g |
| 45% strength NaOH | 0.40 g |
| Demineralized water | 39.10 g |

Greasy ointment

Example 1

| | |
|---|---|
| Active compounds A to Z or $A^1$ to $H^1$ | 1.00 g |
| Ciprofloxacin | 1.00 g |
| Woolwax alcohol | 5.00 g |
| White vaseline to | 100 g |

Dusting powder

Example 1

| | |
|---|---|
| Active compounds A to Z or $A^1$ to $H^1$ | 0.1 g |
| Ciprofloxacin hydrochloride | 0.1 g |
| Lactose to | 100 g |

Shaking mixture

| | |
|---|---|
| Active compounds A to Z or $A^1$ to $H^1$ | 1.0 g |
| Ciprofloxacin | 1.0 g |
| Lanette N | 3.0 g |
| Zinc oxide | 18.0 g |
| Talc | 18.0 g |
| 85% strength glycerol | 18.0 g |
| 96% strength ethanol | 13.2 g |
| Demineralized water | 28.8 g |

The ciprofloxacin, zinc oxide and talc are suspended in a solution of the other auxiliaries.

Paste

| | |
|---|---|
| Active compounds A to Z or $A^1$ to $H^1$ | 10.0 g |
| Ciprofloxacin | 10.0 g |
| Wheat starch | 20.0 g |
| Zinc oxide | 20.0 g |
| White vaseline | 50.0 g |

The solids are dried at 40° C. for 4 hours, sieved and suspended in the molten vaseline and the suspension is stirred until cold.

Polyethylene glycol ointment

| | |
|---|---|
| Active compounds A to Z or $A^1$ to $H^1$ | 0.50 g |
| Ciprofloxacin | 0.50 g |
| Polyethylene glycol 300 | 49.75 g |
| Polyethylene glycol 1500 | 49.75 g |

The ciprofloxacin is suspended in the melt of the polyethylene-glycols. The suspension is then stirred until cold.

Greasy ointment

| | |
|---|---|
| Active compounds A to Z or $A^1$ to $H^1$ | 1.00 g |
| Microfine ciprofloxacin | 1.00 g |
| Methyl p-hydroxybenzoate | 0.07 g |
| Propyl p-hydroxybenzoate | 0.03 g |
| Heavy liquid paraffin | 15.00 g |
| Woolwax alcohol ointment | 83.90 g |

The ciprofloxacin is introduced into the molten greasy phase. The mixture is then cooled, with stirring.

Dusting powder

| | |
|---|---|
| Active compounds A to Z or $A^1$ to $H^1$ | 0.01 g |
| Ciprofloxacin, sodium salt | 0.01 g |
| Non-swellable rice starch | 99.99 g |

Water-in-oil ointment

| | |
|---|---|
| Active compounds A to Z or $A^1$ to $H^1$ | 2.00 g |
| Ciprofloxacin | 2.00 g |
| Protegin X | 22.00 g |
| Beeswax | 3.00 g |
| Isopropyl myristate | 1.50 g |
| Medium-chain triglycerides | 1.50 g |
| Mixture of alkyl-branched fatty acid esters | 2.00 g |
| Glycerol | 3.00 g |
| Demineralized water | 65.00 g |

Other examples of formulations with a particular degree of penetration.

Example 1

| | |
|---|---|
| Triamcinolone acetonide (triamcinolone below) | 1.0% |
| Ciprofloxacin hydrochloride | 1.0% |
| Propylene glycol (1,2-propanediol) | 94.0% |
| Methyl laurate | 4.0% |

Example 2

| | |
|---|---|
| Hydrocortisone acetate | 1.0% |
| Ciprofloxacin lactate | 1.0% |
| Propylene glycol (1,2-propanediol) | 93.0% |
| Oleic acid | 5.0% |

Example 3

| | |
|---|---|
| Betamethasone valerate | 0.5% |
| Ciprofloxacin | 0.5% |
| Propylene glycol (1,2-propanediol) | 93.0% |

Example 4

| | |
|---|---|
| Fluocinolone acetonide | 0.5% |
| Ciprofloxacin | 0.5% |
| Propylene glycol (1,2-propanediol) | 94.0% |
| Monoolein | 5.0% |

-continued

| | |
|---|---|
| Oleyl alcohol | 6.0% |

Example 5

| | |
|---|---|
| Flupamesone | 0.5% |
| Ciprofloxacin | 0.5% |
| Propylene glycol (1,2-propanediol) | 97.0% |
| Myristyl alcohol | 2.0% |

Example 6

| | |
|---|---|
| Triamcinolone | 0.5% |
| Ofloxacin | 0.5% |
| 1,2-Butanediol | 95.0% |
| Methyl laurate | 4.0% |

Example 7

| | |
|---|---|
| Triamcinolone | 0.5% |
| Norfloxacin | 0.5% |
| 1,3-Butanediol | 97.0% |
| Methyl laurate | 2.0% |

Example 8

| | |
|---|---|
| Hydrocortisone acetate | 0.25% |
| Ciprofloxacin | 0.25% |
| 1,2-Butanediol | 97.50% |
| Oleic acid | 2.0% |

Example 9

| | |
|---|---|
| Hydrocortisone acetate | 2.0% |
| Norfloxacin | 2.0% |
| 1,3-Butanediol | 91.0% |
| Oleic acid | 5.0% |

Example 10

| | |
|---|---|
| Betamethasone valerate | 2.0% |
| Pefloxacin, ofloxacin | 2.0% |
| 1,2-Butanediol | 91.0% |
| Oleyl alcohol | 5.0% |

Example 11

| | |
|---|---|
| Fluocinolone acetonide | 5.0% |
| Ciprofloxacin | 5.0% |
| 1,2-Butanediol | 87.0% |
| Monoolein | 3.0% |

Example 12

| | |
|---|---|
| Flupamesone | 1.0% |
| Ciprofloxacin | 1.0% |
| Hydrocortisone acetate | 1.0% |
| Propylene glycol (1,2-propanediol) | 92.0% |
| Myristyl alcohol | 5.0% |

Example 13

| | |
|---|---|
| Desoxycorticosterone | 5.0% |
| Ciprofloxacin, ofloxacin | 5.0% |
| Propylene glycol (1,2-propanediol) | 85.0% |
| Oleic acid | 5.0% |

Example 14

| | |
|---|---|
| Prednisolone | 5.0% |
| Ciprofloxacin | 5.0% |
| Propylene glycol (1,2-propanediol) | 86.0% |
| Myristyl alcohol | 4.0% |

Example 15

| | |
|---|---|
| Prednisone | 2.0% |
| Ciprofloxacin | 2.0% |
| 1,2-Butanediol | 52.0% |
| Oleic acid | 4.0% |
| Ethanol | 40.0% |

Example 16

| | |
|---|---|
| Methylprednisolone | 4.0% |
| Ciprofloxacin | 4.0% |
| 1,3-Butanediol | 51.0% |
| Oleyl alcohol | 1.0% |
| Isopropanol | 40.0% |

It will be appreciated that the instant specification and examples are set forth by way of illustration and not limitation, and that various modifications and changes may be made without departing from the spirit and scope of the present invention.

I claim:

1. A topically applicable formulation comprising by weight about 0.05 to 30% of an antibacterially active compound of the formula

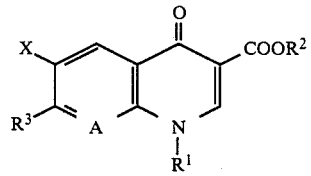

in which

R$^1$ represents methyl, ethyl, propyl, isopropyl, cyclopropyl, vinyl, 2-hydroxyethyl, 2-fluoroethyl, methoxy, amino, methylamino, dimethylamino, ethylamino, phenyl, 4-fluorophenyl or 2,4-difluorophenyl, R² represents hydrogen, alkyl with 1 to 4 carbon atoms or (5-methyl-2-oxo-1,3-dioxol-4-yl)-methyl, R³ represents methyl or a cyclic amino group of the formula

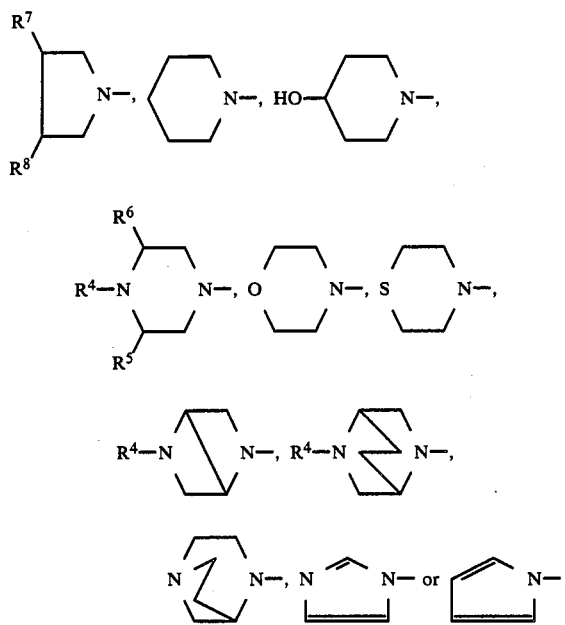

wherein

R⁴ represents hydrogen, alkyl with 1 to 4 carbon atoms, 2-hydroxyethyl, allyl, propargyl, 2-oxopropyl, 3-oxobutyl, phenacyl, formyl, CFCL₂-S-, CFCL₂-SO₂-, CH₃O-CO-S-, benzyl, 4-aminobenzyl or

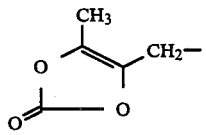

R⁵ represents hydrogen or methyl,

R⁶ represents hydrogen, alkyl with 1 to 4 carbon atoms, phenyl or benzyloxymethyl, R⁷ represents hydrogen, amino, methylamino, ethylamino, aminomethyl, methylaminomethyl, ethylaminomethyl, dimethylaminomethyl, hydroxyl or hydroxymethyl and R⁸ represents hydrogen, methyl, ethyl or chlorine, X represents hydrogen, fluorine, chlorine or nitro and A represents N or C-R⁹, wherein R⁹ represents hydrogen, halogen, such as fluorine or chlorine, methyl or nitro, or A, together with R¹, can also form a bridge with the structure

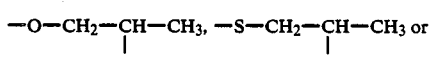

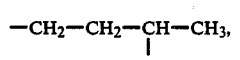

0.01 to 10% of a corticosteroid, and a carrier.

2. A topically applicable formulation according to claim 1, wherein the antibacterially active compound is selected from the group consisting of ciprofloxacin, norfloxacin, perfloxacin, amifloxacin, pirfloxacin, ofloxacin and enoxacin, and the corticosteroid is selected from the group consisting of A beclomethasone dipropionate
B clobetasol propionate
C diflucortolone valerate
D fluocinolone acetonide
E beclomethasone dipropionate
F betamethasone benzoate
G betamethasone dipropionate
H betamethasone valerate
I desonide
J desoxymethasone
K diflorasone diacetate
L diflucortolone valerate
M fluclorolone acetonide
N fluocinolone acetonide
O fluocinonide
P fluocortolone
Q fluprednidene (fluprednylidene) acetate
R flurandrenolone
S halcinonide
T hydrocortisone butyrate
X triamcinolone acetonide
Y clobetasone butyrate
Z flumethasone pivalate
A¹ fluocinolone acetonide
B¹ fluocortine butyl ester
C¹ fluocortolone
D¹ flurandrenalone
E¹ hydrocortisone (urea)
F¹ dexamethasone
G¹ hydrocortisone (alcohol or acetate) and
H¹ methylprednisolone.

3. A topically applicable formulation according to claim 1, in the form of a solution, spray, lotion, gel, ointment, cream, powder, dusting powder spray, paste, suspension, emulsion, foam.

4. A topically applicable formulation according to claim 1, comprising by weight about
(a¹) 0.1 to 20% of an active compound of the formula I,
(a²) 0.01 to 10% of a corticosteroid,
(b) 1 to 40% of a water-soluble gel- or lacquer-forming polymer,
(c) 40 to 98% of an organic water-miscible solvent which evaporates faster than water and in which the polymer does not dissolve, and
(d) 0.1 to 10% of at least one of a plasticizer, suspending auxiliary, antioxidant, spreading agent or dyestuff.

5. A topically applicable formulation according to claim 1, comprising by weight about
(a¹) 0.1 to 5% of an active compound of the formula I,
(a²) 0.02 to 5% of a corticosteroid,
(b) 1 to 20% of a water-soluble gel- or lacquer-forming polymer,
(c) 60 to 90% of an organic water-miscible solvent which evaporates faster than water and in which the polymer does not dissolve, and
(d) 0.1 to 10% of at least one of a plasticizer, suspending auxiliary, antioxidant, spreading agent or dyestuff.

6. A topically applicable formulation according to claim 1, further containing a spreading agent.

7. A composition according to claim 1 in the form of a gel, the carrier including as a gel-forming agent, cellulose ether, polyacrylic acid, polymethacrylic acid, sodium alginate or propylene glycol alginate, sodium amylopectin semiglycolate, alginic acid, gum arabic or guar gum.

8. A composition according to claim 7 further containing a linear high molecular weight polysaccharide as a stabilizing gel-forming agent.

9. A composition according to claim 1 in the form of a suspension having solid particles of 0.1 to 100 μm and a solids content of about 0.5 to 40% by weight.

10. A composition according to claim 1 in the form of an emulsion.

11. A composition according to claim 1 in the form of a solution, the carrier comprising at least one solvent selected from the group consisting of ethanol, isopropyl alcohol, propylene glycol, polyethylene glycol, glycerol, methylcellosolve, cellosolve, an ester, morpholine, dioxane, dimethylsulphoxide, water and cyclohexanone.

* * * * *

UNITED STATES PATENT AND TRADEMARK OFFICE
CERTIFICATE OF CORRECTION

PATENT NO. : 4,844,902

DATED : Jul. 4, 1989

INVENTOR(S) : Grohe

It is certified that error appears in the above-identified patent and that said Letters Patent is hereby corrected as shown below:

| | |
|---|---|
| Title Page, under "U.S. Patent Documents", line 1 | Correct spelling of --Grohe-- |
| Title Page, under "U.S. Patent Documents", line 2 | Correct spelling of --Marples-- |
| Col. 2, line 44 | Delete "topicallys" and substitute --corticosteroids-- |
| Col. 4, line 47 | Delete "the" in first instance and substitute --to-- |
| Col. 5, line 41 | Delete "alcoholk" and substitute --alcohol;-- |
| Col. 6, line 57 | Delete "$C_{18}$" in first instance and substitute --$C_{12}$-- |
| Col. 8, line 35 | Correct spelling of --hydrogenated-- |
| Col. 9, lines 18 and 19 | Delete "to woven fabrics, knitted fabrics and" |
| Col. 10, line 51 | Correct spelling of --corticosteroid-- |
| Col. 12, line 64 | Delete "dispersion" and substitute --dispersing-- |
| Col. 16, line 6 | Correct spelling of --local-- |
| Col. 16, line 15 | Correct spelling of --gonorrhoeae-- |
| Col. 18, line 65 | Delete "100" and substitute --110-- |
| Col. 22, line 26 | Delete "1.00g" |
| Col. 22, line 28 | Delete "3.00 g" and substitute --1.00 g-- |
| Col. 22, line 29 | Insert --3.00 g-- |

UNITED STATES PATENT AND TRADEMARK OFFICE
CERTIFICATE OF CORRECTION

PATENT NO. : 4,844,902
DATED : Jul. 4, 1989
INVENTOR(S) : Grohe

It is certified that error appears in the above-identified patent and that said Letters Patent is hereby corrected as shown below:

Col. 23, line 49    Correct spelling of --hydrocortisone--

Col. 24, line 47    Correct spelling of --light--

Signed and Sealed this

Twenty-seventh Day of November, 1990

Attest:

HARRY F. MANBECK, JR.

Attesting Officer    Commissioner of Patents and Trademarks